US012559741B2

(12) United States Patent
Dai

(10) Patent No.: US 12,559,741 B2
(45) Date of Patent: *Feb. 24, 2026

(54) HIGH DENSITY DISTRIBUTED THREE-DIMENSIONAL ELECTRODE DEVICE

(71) Applicant: Suzhou Etta Biotech Co., Ltd., Jiangsu (CN)

(72) Inventor: Edward Dai, Jiangsu (CN)

(73) Assignee: SUZHOU ETTA BIOTECH CO., LTD., Jiangsu (CN)

( * ) Notice: Subject to any disclaimer, the term of this patent is extended or adjusted under 35 U.S.C. 154(b) by 768 days.

This patent is subject to a terminal disclaimer.

(21) Appl. No.: 17/862,707

(22) Filed: Jul. 12, 2022

(65) Prior Publication Data

US 2022/0340855 A1 Oct. 27, 2022

Related U.S. Application Data

(63) Continuation-in-part of application No. 16/192,077, filed on Nov. 15, 2018, now Pat. No. 11,421,196, which is a continuation of application No. 14/896,902, filed as application No. PCT/CN2014/079391 on Jun. 6, 2014, now abandoned.

(30) Foreign Application Priority Data

Jun. 8, 2013 (CN) .......................... 201310227093.7

(51) Int. Cl.
| | |
|---|---|
| *C12N 13/00* | (2006.01) |
| *C12M 1/42* | (2006.01) |
| *C12N 15/87* | (2006.01) |

(52) U.S. Cl.
CPC ............. *C12N 13/00* (2013.01); *C12M 35/02* (2013.01); *C12N 15/87* (2013.01)

(58) Field of Classification Search
CPC ............................... C12M 35/02; C12N 13/00
See application file for complete search history.

(56) References Cited

U.S. PATENT DOCUMENTS

| | | | |
|---|---|---|---|
| 5,128,257 | A | 7/1992 | Baer |
| 6,352,853 | B1 | 3/2002 | King et al. |
| 6,448,947 | B1 | 9/2002 | Nagai |
| 6,482,619 | B1 | 11/2002 | Rubinsky et al. |
| 10,731,120 | B2 | 8/2020 | Dai |
| 10,982,182 | B2 | 4/2021 | Dai |
| 2004/0167458 | A1 | 8/2004 | Draghai-Akli et al. |
| 2005/0043726 | A1 | 2/2005 | McHale et al. |
| 2005/0089992 | A1 | 4/2005 | Walters et al. |
| 2008/0063866 | A1 | 3/2008 | Allen et al. |
| 2013/0052711 | A1 | 2/2013 | Chen |

FOREIGN PATENT DOCUMENTS

| | | | | |
|---|---|---|---|---|
| CN | 101563132 A | 10/2009 | | |
| CN | 101693875 A | 4/2010 | | |
| CN | 102680526 A | 9/2012 | | |
| CN | 103275874 A | 9/2013 | | |
| KR | 10-2007-0089374 A | 8/2007 | | |
| WO | 98/56893 | 12/1998 | | |
| WO | 99/37358 | 7/1999 | | |
| WO | WO-9943782 A1 * | 9/1999 | ........... | C12M 35/02 |
| WO | 0004949 A1 | 2/2000 | | |
| WO | 2005044983 A2 | 5/2005 | | |
| WO | 2005044983 A3 | 5/2005 | | |
| WO | 2009/091578 A1 | 7/2009 | | |
| WO | 2013/066427 A1 | 5/2013 | | |

OTHER PUBLICATIONS

International Searching Authority, International Search Report and Written Opinion for PCT/CN2014/079391, Sep. 5, 2014.

* cited by examiner

*Primary Examiner* — David W Berke-Schlessel
*Assistant Examiner* — Susan E. Fernandez
(74) *Attorney, Agent, or Firm* — Schmeiser, Olsen & Watts LLP

(57) ABSTRACT

A high-density distributed three-dimensional electrode device and an associated electroporation method is provided. The method includes applying an electric pulse of a first polarity to a first group of electrodes while simultaneously applying an electrical pulse of a second polarity to a remaining group of electrodes, and then applying an electric pulse of the first polarity on a second group of electrodes while simultaneously applying an electric pulse of the second polarity to the remaining groups of electrodes. The electrodes receiving the electric pulse of the first polarity being surrounded by the electrodes receiving the electric pulse of the second polarity, and the first polarity and the second polarity are opposite.

9 Claims, 5 Drawing Sheets

HIGH DENSITY DISTRIBUTED THREE-DIMENSIONAL ELECTRODE DEVICE

CROSS REFERENCE TO RELATED APPLICATIONS

This application is a continuation-in-part application of U.S. application Ser. No. 16/192,077, having a filing date of Nov. 15, 2018, which is a continuation application of U.S. application Ser. No. 14/896,902, having a filing date of Dec. 8, 2015, which claims priority to PCT/CN2014/079391 having a filing date of Jun. 6, 2014, which claims priority to CN 201310227093.7, having a filing date of Jun. 8, 2013, the entire contents all of which are hereby incorporated by reference.

FIELD OF TECHNOLOGY

The following relates to a cell electroporation technique, in particular a three-dimensional electrode device for electroporation.

BACKGROUND

Since the 1970s, the electroporation technique was used to insert molecules into animal cells or plant cells. It is proved by researchers that exposing a cell to a short-lasted high-voltage electric field may enable formation of pathways through the cell membrane, and macromolecules such as proteins and DNAs may enter into the cell through those pathways. Those pathways are referred as electroporation pores which are permeability increased zone caused by a local fracture of cell membrane resulted from high voltage electric field. Although the existing times of the pores are brief, it is enough to satisfy the requirement of the macromolecules such as plasmid DNA molecules entering into the cell. The cell may tolerate the formation of the pores; however, the cell may be killed by the processes of the formation and the molecules introduced thereby if the formed pores are too much and overlarge.

At the earliest, the electroporation is carried out by using the simplest capacitor with parallel-plate, and a substantially homogeneous electric field may be formed between the electrodes opposite to each other. The cell suspension prepared for electroporation and the molecules which the operator wants to introduce are mixed and placed between the two electrodes, and a short-time high voltage electric pulse is applied to the electrodes by one or more times such that the result of introducing the molecules into cells by electroporation can be achieved. However, the distance between the parallel-plate electrodes is large, the required voltage is usually up to several thousand volts, thus generating of cathode effect is inevasible, which has a huge damage to the cells.

Although the planar electrodes arose later solve the negative effect brought by the over high voltage, they are not suitable for high throughput experiment operations due to that the planer electrodes can process a very small amount of cells every time. Three-dimensional electrodes easily penetrate into tissues and living bodies, and usually use for electroporation in clinics for tumor tissues or living tissues, the electroporation efficiency of which is not high, and there is no related report of extracorporeal cell electroporation such as electroporation aimed at suspended cells or attached cells via three-dimensional electrodes.

SUMMARY

An aspect relates to an electroporation method for cells in a fluid to reduce a death rate of cells, especially suitable for being used in vitro cell suspension, which can reduce the death rate (or, mortality rate) of cells.

Embodiments of the present invention provide a high-density distributed three-dimensional electrode device, which has a simple structure and is easy to manufacture.

To solve the above-mentioned technical problems, embodiments of the present invention provides a high-density distributed three-dimensional electrode device, comprising an electrode array and an electrode fixing assembly on which the electrode array is fixed, the electrode array comprising a plurality of electrodes divided into at least two groups, an electric pulse of a first polarity and an electric pulse of a second polarity are respectively applied on the at least two groups according to a time period, wherein the first polarity and the second polarity are different, and the electrodes corresponding to the electric pulse of the second polarity are distributed around the electrodes corresponding to the electric pulse of the first polarity.

In an embodiment of the present invention, the plurality of electrodes in the electrode array is arranged according to an equilateral polygon, and the distances between every two adjacent electrodes in the electrode array are equal.

In an embodiment of the present invention, a shape of the electrode array is an equilateral hexagon formed by several equilateral triangles, and the electrodes are located at the vertexes of the equilateral triangles.

In an embodiment of the present invention, the first polarity is positive polarity, and the second polarity is negative polarity.

In an embodiment of the present invention, the first polarity is negative polarity, and the second polarity is positive polarity.

In an embodiment of the present invention, the diameter of the electrodes is 0.01-1.2 mm, the distance between the center points of the two adjacent electrodes is 0.1-2.4 mm, the number of the electrodes is more than 5, and the number is preferred to be more than 19. The material of the electrodes is stainless steel.

In an embodiment of the present invention, the diameter of the electrodes is 0.1-0.4 mm, the distance between the center points of the two adjacent electrodes is 0.2-1.5 mm, and the number of the electrodes is more than 36. The diameter of the electrodes is 0.3 mm, the distance between the center points of the two adjacent electrodes is 1 mm, and the number of the electrodes is 37.

In an embodiment of the present invention, the electrode fixing assembly comprises an electrode connecting circuit board and an electrode positioning board, the electrode connecting circuit board connects the electrodes applied with the electric pulse of the same polarity together via a wire thereon, and the electrodes are inserted into the electrode positioning board.

In an embodiment of the present invention, the electrodes in the electrode array are divided into several groups, and the electrodes in the same group are only applied with the electric pulse of the same polarity, wherein one of the groups is applied with the electric pulse of positive polarity, the rest groups are applied with the electric pulse of negative polarity, and then another one of the groups is applied with the electric pulse of positive polarity, the rest groups are applied with the electric pulse of negative polarity, and alternately in this way, the obtained electric field may achieve a homogeneous electric field by superposition.

The beneficial effects of embodiments of the present invention are that: the high density distributed three-dimensional electrode device of embodiments of the present invention employ grouped reused electrodes; can compensate for the unevenness of the electric field caused by the three-dimensional electrode at the greatest extent; can process milliliter level of cells once; can be used in both pore plate devices and flow devices; requires a small electroporation voltage due to a small distance between the electrodes, avoiding the damage to the cells from the high voltage; low cost; is a cell electroporation device with high throughput and high efficiency.

BRIEF DESCRIPTION

Some of the embodiments will be described in detail, with references to the following Figures, wherein like designations denote like members, wherein.

Wherein reference numbers and corresponding parts are as follow: 1—electrode array, 2—electrode positioning board, 3—electrode connecting circuit board.

DETAILED DESCRITPION

Figure 1:
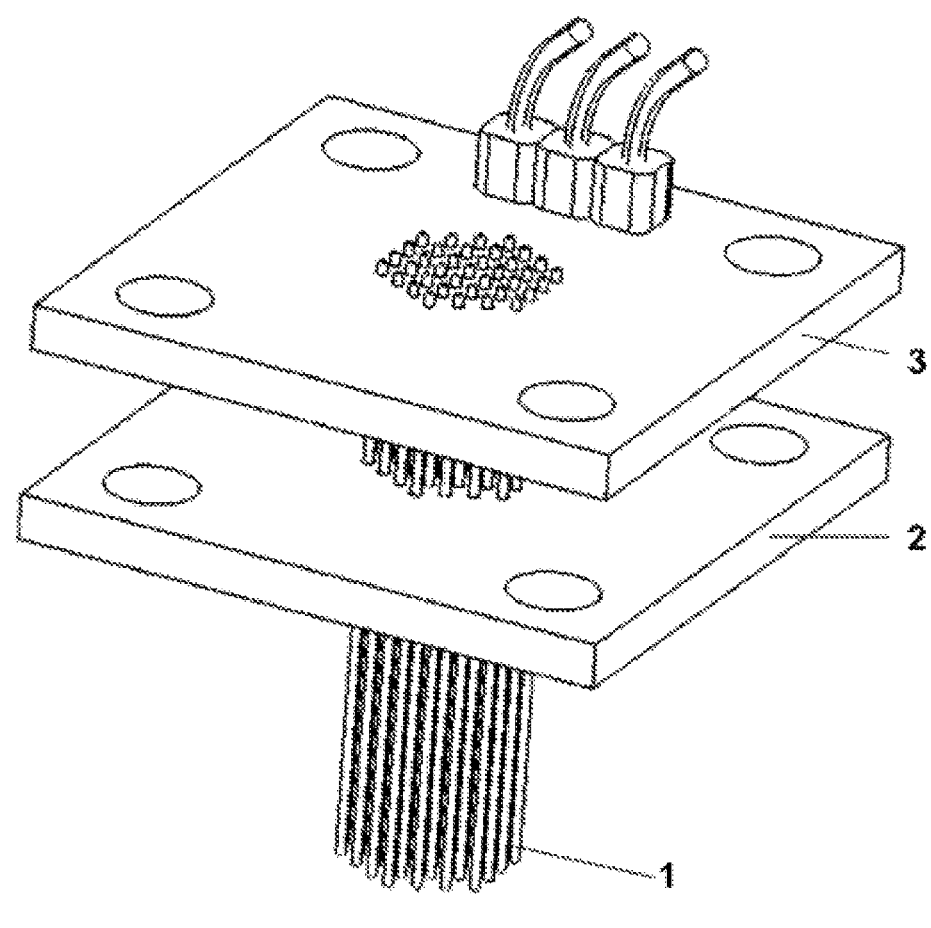
FIG. 1 is a structure schematic diagram of a preferable embodiment of a high-density distributed three-dimensional electrode device.
Figure 2:
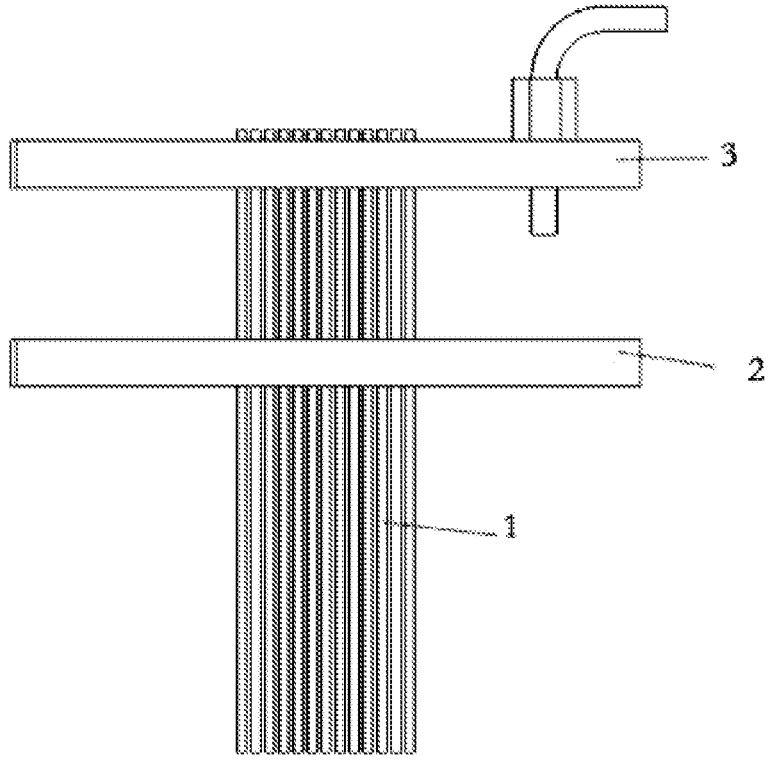
FIG. 2 is a front view of the high-density distributed three-dimensional electrode device shown in FIG. 1.
Figure 3:
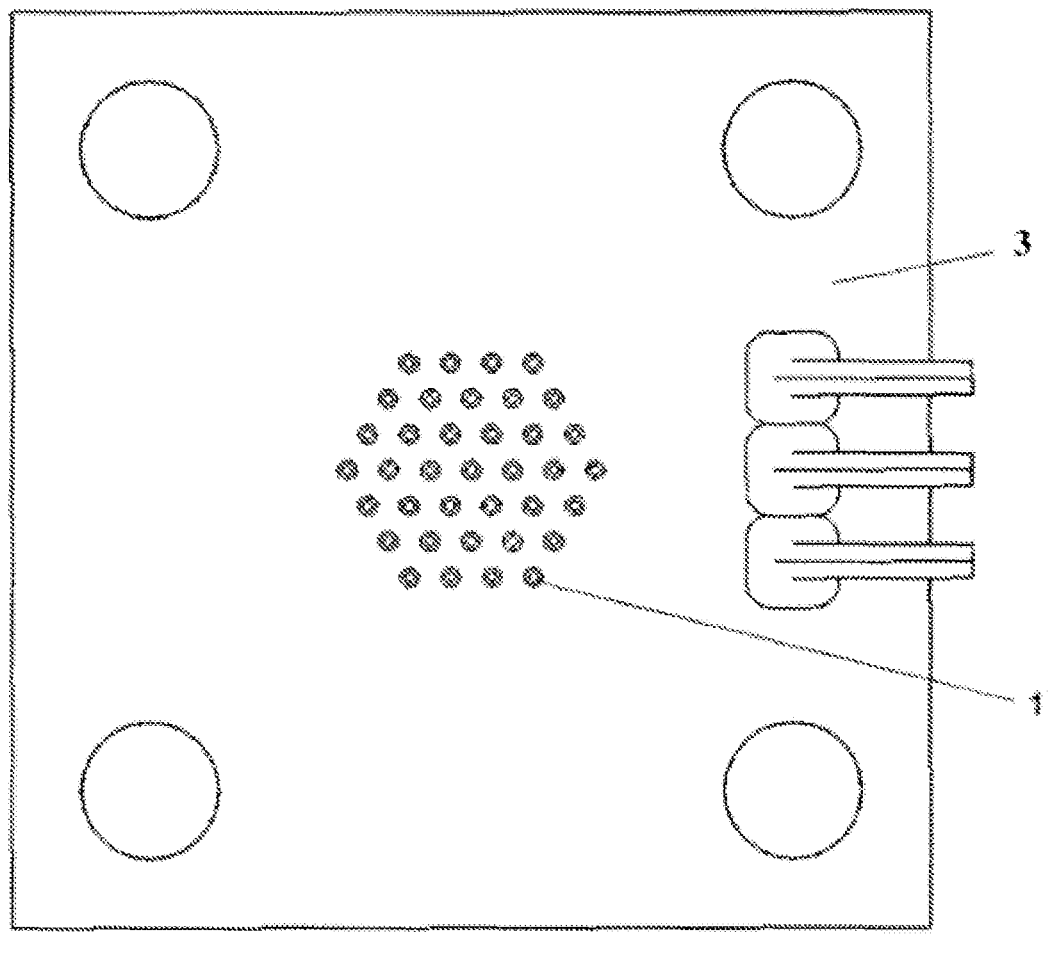
FIG. 3 is a top view of the high-density distributed three-dimensional electrode device shown in FIG. 1.

The embodiments of the present invention are explained in the followings in details combining with the accompanying drawings so that the advantages and features of embodiments of the present invention can be easily understood by the skilled persons in the art, and at the same time it clearly defines the protected scope of embodiments of the present invention.

Embodiment 1

Referring to FIG. 1, FIG. 2, FIG. 3 and FIG. 4, embodiments of the present invention provide a high-density distributed electrode device, comprising an electrode array 1 and an electrode fixing assembly on which the electrode array 1 is fixed.

The electrode array 1 is formed by 37 solid cylinder electrodes, and the arrangement rules are as follow: all the electrodes are arranged to be an equilateral hexagon shaped structure, the distances between two adjacent electrodes are equal, the inside of the equilateral hexagon shape is divided into several small equilateral triangle units by taking the distances between two adjacent electrodes as side length, and one electrode is placed at each vertex of the equilateral triangle units, that is, all the electrodes are divided into three groups, Group I, II and III, and vertexes of each equilateral triangle unit respectively belong to Group I, II and III.

The outer diameter of the equilateral hexagon of the electrode array 1 is matched up with the plate holes of a perforated plate, and a distance between the center points of two adjacent electrodes is 1 mm. The distance between two electrodes may affect the voltage during electroporation, and can be adjusted as required. The electrodes are inserted into the perforated plate and have a distance of 0.1 mm-1 mm from the bottom of the perforated plate.

The diameter of the electrodes is 0.3 mm, and both too large and too small diameters of the electrodes may affect the effect of the electroporation. When the diameters are too large, the effective area of electric field may be reduced, resulting in a decrease on the number of cells dealed with by electroporation, and going against high throughput of cell electroporation.

When the diameters are too small, the electrodes are easily bended resulting in a large increase of the manufacturing cost.

The material of the electrodes may be optionally selected from metals and other electric conductive materials, wherein the stainless steel is an excellent material for electrodes. The stain steel material possesses favorable bio-compatibility, is easy to clean and not easy to be oxidized, easy to form relatively long electrodes, and is able to be mass produced and be reused for multiple times without affecting the conduction properties thereof.

The electrode fixing assembly comprises an electrode positioning board 2 and an electrode connecting circuit board 3, the electrodes are positioned by going through the electrode positioning board 2 and connected to the electrode connecting circuit board 3, and the electrode connecting circuit board 3 connects the electrodes applied with the electric pulse of the same polarity together via a wire thereon. Due to that the electrodes are relatively long and the electroporation has a very high accuracy requirement for the distance between the electrodes, the electrode positioning board 2 is employed to position the electrodes in electroporation experiments. The electrode positioning board 2 can confine and position the electrodes along a long distance due to a thickness thereof is about 1 cm, and therefore, the electrodes can be controlled accurately to reach the bottom of the perforated plate. A support structure of the high density distributed three-dimensional electrode device may be easily extended to form electrode networks of any combination array such as 2*2, 1*4, 12*8 etc., and such flexible and varied combinations may be compatible with the perforated plate structure at the greatest extent, being convenient for user.

The electrode connecting circuit board 3 connects the electrodes in the same group together by welding connection, conducting adhesive or other electrical connecting manner such as printed circuit board and another component which can connect regulation lines. The electrode positioning board 2 is used for positioning the electrodes which are vimineous and easily bended. Therefore, in the embodiments of FIGS. 1-2, the electrode positioning board 2 is arranged approximately at the middle of the electrodes for positioning. The use of the electrode positioning board 2 can reduce the inconformity of the distances between the electrodes and thus improve the homogeneity of the electric field.

The high-density distributed three-dimensional electrode device may be a monoporate device, and 4, 96 or more of this device can be used to form a group to cooperate with a multi-well plate commonly used in biology.

The electroporation method of the high-density distributed three-dimensional electrode device in the present embodiment is: during the electroporation, first assign Group I as positive electrodes and Group II, III as negative electrodes the electric pulse is applied, then assign Group II as positive electrodes and Group I, III as negative electrodes the electric pulse is applied, and then assign Group III as positive electrodes and Group I, II as negative electrodes the electric pulse is applied.

For certain kind of cells, pores may appear on the cell membranes when the electric field is higher than a certain threshold. The death rate of the cells may increase as the intensity of the electric field gradually increases. To ensure a high electroporation rate and low mortality rate of the cells, it is desired to accurately control the electric field to be the threshold electric field of the electroporation.

As long as the homogeneous electric field intensity is controlled to be the optimal electroporation voltage of the electroporation, cells in the whole effective area may experience electroporation at the greatest extent. It can be seen that grouping and reusing compensate for the unevenness of the electric field caused by single group, increases the electroporation efficiency, and thus it can be determined that such kind of combination of electric fields has a much higher electroporation efficiency than the conventional electroporation.

The high-density distributed three-dimensional electrode device may carry out electroporation for many cell lines in suspension or in adherence. 12 kinds of cells, 7 HEK-293A, Hela, MCF-7, A-375, Neuro-2A, U251, C2C12, 3T3-L1, CHO, MDCK, HL-60, HUVEC, are chosen to undergo electroporation, and GFP molecules are used as marker. The GFP molecules may enter into the cells and synthesize fluorescent substances in the cells if the cells are electroporated, and the synthesized fluorescent substances may glow green fluorescence under a fluorescent field so that the electroporation rate of the cells may be obtained from the number of cells in the fluorescent field divided by the total number of cells, that is to say, the higher the fluorescence intensity of the same density of cells is, the higher the efficiency of the electroporation is.

The high-density distributed three-dimensional electrode device according to embodiments of the present invention may be applied in a flow device. By placing the high-density distributed three-dimensional electrode device in the flow device, the cells evenly distributed and flowing along with the flowing fluid may accept an optimal electroporation stimulation conditions when the cells experience the control of the flowing rate and pulse stimulation during passing through the electrode array, the electroporation stimulation conditions comprising the voltage amplitude value of pulse, pulse width, pulse interval, pulse number and electrode swapping control. In a continuous flowing system, except that the time when the pulses are applied to the electrodes and the time when the cells begin to flow among the electrodes need to be harmonized, the pulses and the flowing of the cell do not need a harmonization of "duration handling" between them.

The high-density distributed three-dimensional electrode device according to embodiments of the present invention both has a advantage of continuous flow electroporation, in particularly being able to carry out a high-throughput electroporation for cells in a sterile closed system, and is also able to ensure that each of the cells is subjected with optimal number of pulses and most even electric field to improve the electroporation efficiency and low down the death rate.

Embodiment 2

Figure 5:
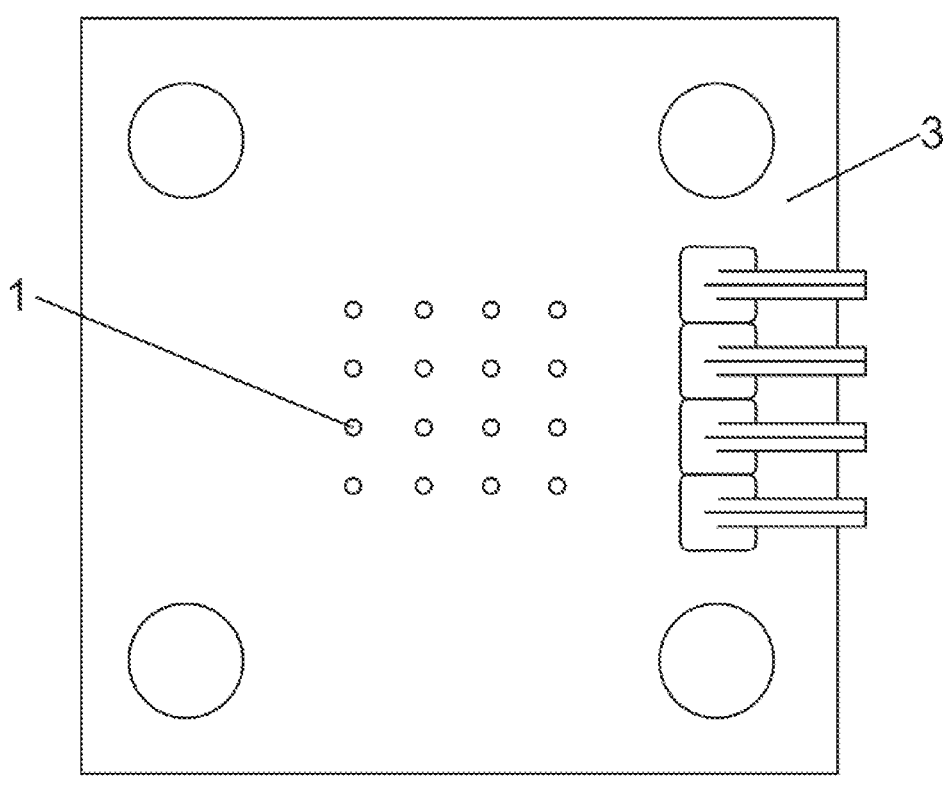
FIG. 5 is a top view of a high-density distributed three-dimensional electrode device of a second preferable embodiment.
Figure 6:
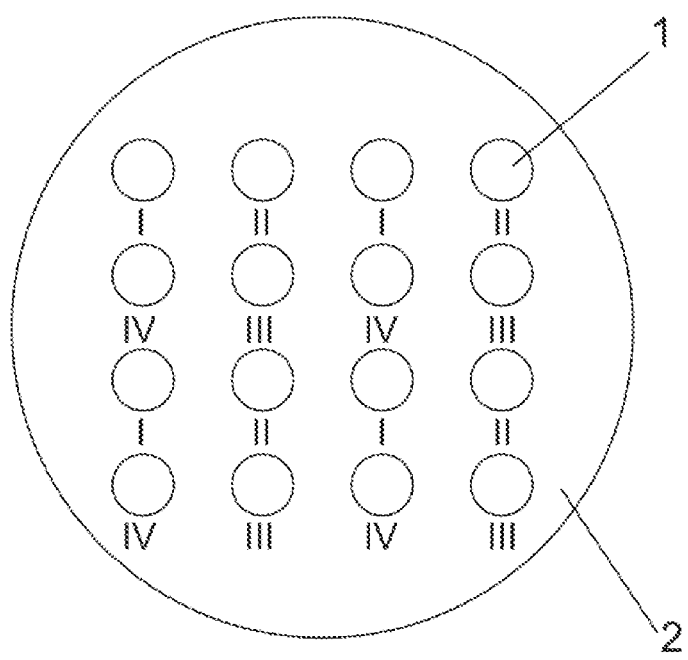
FIG. 6 is a topological structure diagram of an electrode array in the high-density distributed three-dimensional electrode device shown in FIG. 5.

As shown in FIGS. 5 and 6, the high-density distributed three-dimensional electrode device according to present embodiment is similar to that of Embodiment 1, and differing in the arrangement of the electrode array. In present embodiment, the arrangement rule of the electrode array is as follow: all the electrodes are arranged to form an equilateral quadrangle shaped structure, the distances between the adjacent two electrodes are equal, the inside of the equilateral quadrangle is divided into several smaller square units by taking the distances between the adjacent two electrodes as side length, and one electrode is placed at each vertex of the squares. All the electrodes are divided into four groups, Group I, II, III, and IV, and vertexes of each square belong to Group I, II, III, and IV respectively. These groups take turns to be applied with electric pulse in the way that one of the groups is assigned as positive electrodes and the rest groups as negative electrodes.

As shown in FIG. 6, the electroporation method by using the three-dimensional electrode device comprising:

(i) applying the positive electrical pulse to the first group I, and simultaneously applying the negative electrical pulse to the second group II, the third group III and the fourth group IV, wherein each electrode of the first group I is surrounded by electrodes of the second group II, the third group III and the fourth group IV;

(ii) subsequently applying the positive electrical pulse to the second group II and simultaneously applying the negative electrical pulse to the first group I, the third group III and the fourth group IV, wherein each electrode of the second group II is surrounded by electrodes of the first group I, the third group III and the fourth group IV;

(iii) subsequently applying the positive electrical pulse to the third group III and simultaneously applying the negative electrical pulse to the first group I, the second group II and the fourth group IV, wherein each electrode of the third group is III surrounded by electrodes of the first group I, the second group II and the fourth group IV; and (iv) subsequently applying the positive electrical pulse to the fourth group IV and simultaneously applying the negative electrical pulse to the first group I, the second group II and the third group III, wherein each electrode of the fourth group IV is surrounded by electrodes of the first group I, the second group II and the third group III.

Wherein, the three-dimensional electrode device is placed in a flow device in which the cells flow along with the fluid. The steps are performed sequentially and cyclically to achieve a homogeneous electric field by superposing the resulted electric fields. The method could be used for in vitro cell suspension, which can reduce mortality rate of cells.

Embodiment 3

The high-density distributed three-dimensional electrode device provided by the present embodiment is similar to that of Embodiment 1, differing in that the arrangement of the electrode array is as followings: all the electrodes are arranged to form an equilateral hexagon structure, the distances between the adjacent two electrodes are equal, the inside of the equilateral hexagon is divided into several smaller equilateral hexagon units by taking the distances between the adjacent two electrodes as side length, and one electrode is placed at each vertex of the hexagon units, i.e., all the electrodes are divided into six groups, Group I, II, III, IV, V, and VI, and vertexes of each hexagon unit respectively belong to Group I, II, III, IV, V, and VI, and these groups take turns to be applied with the electric pulse in the way that one of the groups is assigned as positive electrodes and the rest groups as negative electrodes. The arrangement of the electrode array of the present embodiment may be presented

7

Figure 4:
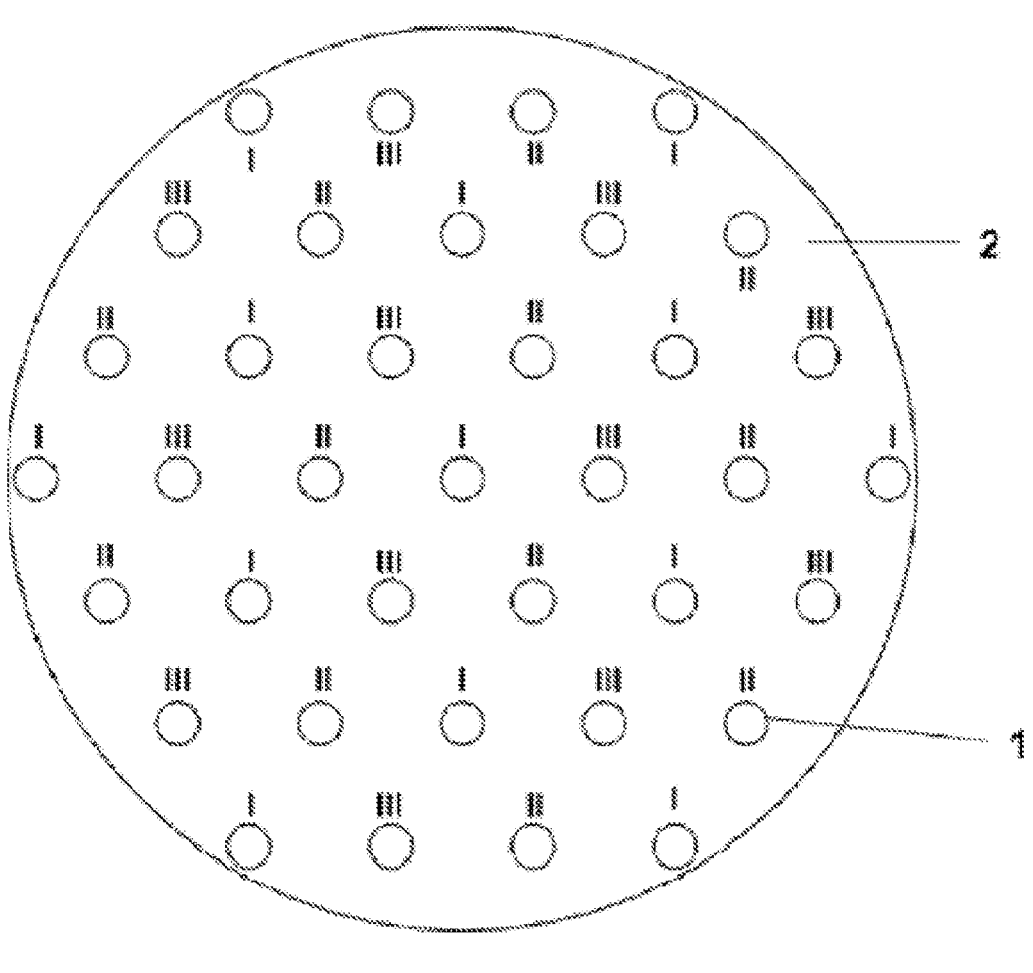
FIG. 4 is a topological structure diagram of an electrode array in the high-density distributed three-dimensional electrode device shown in FIG. 1.

8 by slightly modifying the structure of Embodiment 1 shown in FIG. 4, and therefore no more figures are submitted.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. An electroporation method for cells in a fluid to reduce a death rate of cells, the method comprising:

placing a three-dimensional electrode device in a flow device in which the cells flow along with the fluid, wherein the electrode device comprises an electrode array comprising a plurality of needle-shaped electrodes divided into leastfour groups including a first group of electrodes, a second group of electrodes, a third group of electrodes, and a fourth group of electrodes; and an electrode fixing assembly on which the electrode array is fixed;

simultaneously applying electric pulses of positive polarity to the first group of electrodes and electric pulses of negative polarity to the second, third, and fourth groups of electrodes, wherein each electrode of the first group is surrounded by electrodes of the second, third, and fourth groups;

subsequently applying positive electrical pulses to the second group and simultaneously applying negative electrical pulses to the first group, the third group and the fourth group, wherein each electrode of the second group is surrounded by electrodes of the first group, the third group and the fourth group;

subsequently applying positive electrical pulses to the third group and simultaneously applying negative electrical pulses to the first group, the second group and the fourth group, wherein each electrode of the third group is surrounded by electrodes of the first group, the second group and the fourth group; and subsequently applying positive electrical pulses to the fourth group and simultaneously applying negative electrical pulses to the first group, the second group and the third group, wherein each electrode of the fourth group is surrounded by electrodes of the first group, the second group and the third group;

wherein the steps are performed sequentially and cyclically to achieve a homogeneous electric field by superposing the resulting electric fields.

2. The electroporation method of claim 1, wherein a diameter of the electrodes is 0.01-1.2 mm.

3. The electroporation method of claim 1, wherein a diameter of the electrodes is 0.1-0.4 mm.

4. The electroporation method of claim 1, wherein a diameter of the electrodes is 0.3 mm.

5. The electroporation method of claim 1, wherein the plurality of electrodes in the electrode array is arranged according to an equilateral polygon, and distances between every two adjacent electrodes in the electrode array are equal.

6. The electroporation method of claim 5, wherein a shape of the electrode array is an equilateral quadrangle, and the electrodes are located at vertices of the equilateral quadrangle.

7. The electroporation method of claim 1, wherein a material of the electrodes comprises stainless steel.

8. The electroporation method of claim 1, wherein the electrode fixing assembly comprises an electrode connecting circuit board and an electrode positioning board, wherein the electrode connecting circuit board connects the electrodes applied with electric pulses of a same polarity, and the electrodes reside within the electrode positioning board.

9. The electroporation method of claim 1, wherein the electrode fixing assembly comprises an electrode positioning board and an electrode connecting circuit board, wherein the electrodes are positioned by going through the electrode positioning board to reduce inconformity of distances between the electrodes, and the electrodes are connected to the electrode connecting circuit board.

* * * * *